United States Patent
Kawasaki et al.

(10) Patent No.: US 7,144,842 B2
(45) Date of Patent: Dec. 5, 2006

(54) HERBICIDE COMPOSITIONS AND WEEDKILLING METHOD USING THE SAME

(75) Inventors: Hiroshi Kawasaki, Tokyo (JP); Takeshige Miyazawa, Tokyo (JP); Osamu Watanabe, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 208 days.

(21) Appl. No.: 10/518,465

(22) PCT Filed: Jul. 23, 2003

(86) PCT No.: PCT/JP03/09334

§ 371 (c)(1),
(2), (4) Date: Dec. 22, 2004

(87) PCT Pub. No.: WO2004/010784

PCT Pub. Date: Feb. 5, 2004

(65) Prior Publication Data

US 2005/0250646 A1   Nov. 10, 2005

(30) Foreign Application Priority Data

Jul. 25, 2002  (JP) ............................ 2002-215979

(51) Int. Cl.
A01N 57/02 (2006.01)
A01N 47/22 (2006.01)
A01N 47/36 (2006.01)
A01N 43/54 (2006.01)
A01P 13/02 (2006.01)

(52) U.S. Cl. .................. 504/128; 504/134; 504/136

(58) Field of Classification Search ................ 504/128, 504/134, 136, 243
See application file for complete search history.

(56) References Cited

FOREIGN PATENT DOCUMENTS

JP  2000-256109  9/2000
JP  2000-281513  10/2000

*Primary Examiner*—S. Mark Clardy
(74) *Attorney, Agent, or Firm*—Wenderoth, Lind & Ponack, L.L.P.

(57) ABSTRACT

The invention provides a herbicide composition consisting of 2-[(4,6-dimethoxypyrimidin-2-yl)hydroxy-methyl]-6-methoxymethyl-N-difluoromethanesulfonylanilide as the component (A) and any compound selected from more than 20 kinds of specific compounds such as orbencarb and the like as the component (B), heretofore not combined with the component (A) compound. Dispensation of the herbicide composition to paddy fields, lawns, dry fields, or non-agricultural lands gives excellent weed-controlling effects on a variety of weeds and causes no or little phytotoxicities on valuable cultivated plants.

23 Claims, No Drawings

HERBICIDE COMPOSITIONS AND WEEDKILLING METHOD USING THE SAME

TECHNICAL FIELD

The invention relates to an innovative herbicide composition and a method for weed-controlling by using the same, more particularly, to an innovative herbicide composition capable of effectively preventing weed growth and removing various types of weeds growing in paddy fields, lawns, dry fields, or non-agricultural lands, above all, in irrigated paddy fields even only by one time dispensation without inhibiting growth of valuable cultivated plants such as rice, barley and wheat, etc., lawn grasses and the like and a method for weed-controlling grasses out of paddy fields, lawns, dry fields, or non-agricultural lands by dispensing the herbicide composition.

BACKGROUND ART

Various kinds of herbicides have been developed so far and have contributed to agricultural productivity and labor-saving. However, since there are some kinds of herbicides which have been used so many years, some weeds have become resistant to them and hardly destroyable weeds against which those herbicides are not or little effective have been increasing and therefore, it has been highly expected to develop herbicides having a wide herbicide spectrum and effective even against these hardly destroyable weeds.

Further, conventional herbicides often cause pollution of soil and ambient environmental pollution and, in order to prevent such environmental pollution, development of herbicides highly active and effective even in a small amount of use has been desired.

Besides, to deal with uneven propagation of weeds for a long period, herbicides excellent in residual effectiveness, effective even by dispensation in a wide range of periods before development of weeds until the growing period and having a wide range of proper dispensing time have been expected to be available.

Moreover, it is well known that with respect to use of conventional herbicides, phytotoxicities are sometimes caused on cultivated plants depending on a variety of factors relative to weather conditions such as temperature, wind, light, and the like; soil conditions such as soil properties, organic compound contents in soil, and the like; planting management conditions such as shallow transplantation depth, use of fragile and too long seedling, deep water control and the like; chemical agent dispensation conditions such as uneven spraying, excess spraying of herbicides and the like, appearance of herbicides highly safe and free from a risk of occurrence of damages on cultivated plants in any conditions has been desired.

DISCLOSURE OF THE INVENTION

The present invention aims to provide a herbicide composition, especially, a herbicide composition for removing weeds growing in paddy fields, lawns, dry fields, or non-agricultural lands and a weed-controlling method using the same for removing weeds out of paddy fields, lawns, dry fields, or non-agricultural lands.

On the basis of enthusiastic investigations made to satisfy the above-mentioned expectations, the inventors of the invention have found that when 2-[(4,6-dimethoxypyrimidin-2-yl)hydroxymethyl]-6-methoxymethyl-N-difluoromethanesulfonyl-anilide, which is known as an effective component of a herbicide, is used singly, no effective weed-controlling on weeds grown to an advanced state or perennial weeds growing in paddy fields and the like is obtained unless it is used in a high concentration and therefore, phytotoxicities are caused on cultivated plants such as rice, while unexpectedly, only a single dispensation of a low concentration of it in combination with certain kinds of compounds can prevent growth of a wide range of weeds growing in paddy fields, lawns, dry fields, or non-agricultural lands or remove them over a long time and that valuable cultivated plants such as rice, barley and wheat, etc., and lawn grasses are not or little damaged and based on the findings, inventors have accomplished the invention.

That is, the invention provides a herbicide composition comprises, as effective components, (A) 2-[(4,6-dimethoxypyrimidin-2-yl)hydroxymethyl]-6-methoxymethyl-N-difluoromethanesulfonylanilide and (B) a compound selected from the group consisting of S-2-chlorobenzyl diethylthiocarbamate (orbencarb), S-2-benzenesulfonamidoethyl O,O-diisopropyl phosphorodithioate (bensulide), methyl sulfanilylcarbamate (asulam), 3',4'-dichloropropionanilide (propanil), ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl), 1-(2-methylcyclohexyl)-3-phenylurea (siduron), 5-dipropylamino-α,α,α-trifluoro-4,6-dinitro-o-toluidine (prodiamine), N-(1-ethylpropyl)-2,6-dinitro-3,4-xylidine (pendimethalin), N-butyl-N-ethyl-α,α,α-trifluoro-2,6-dinitro-p-toluidine (benfluralin), butyl (R)-2-[4-(4-cyano-2-fluorophenoxy)phenoxy]propionate (cyhalofop-butyl), ethyl (R)-2-[4-(6-chlorobenzoxazol-2-yloxy)phenoxy]propionate (fenoxaprop-(P)-ethyl), ethyl(±)-2-[4-(6-chlorobenzoxazol-2-yloxy)phenoxy]propionate (fenoxaprop-ethyl), 2-{1-[2-(4-chlorophenoxy)prop-oxyimino]butyl}-3-hydroxy-5-(thian-3-yl)cyclohex-2-enone (profoxydim), (±)-(EZ)-2-(1-ethoxyiminobutyl)-5-[2-(ethylthio)propyl]-3-hydroxycyclohex-2-enone (sethoxydim), benzophenone O-[2,6-bis(4,6-dimethoxypyrimidin-2-yloxy)benzoyl]oxime (pyribenzoxim), (1RS,2SR,4SR)-1,4-epoxy-p-menth-2-yl 2-methylbenzyl ether (cinmethylin), 3,7-dichloroquinoline-8-carboxylic acid (quinclorac), N-(4-methoxy-6-methyl-1,3,5-triazin-2-yl)-N'-(2-methoxycarbonylphenylsulfonyl)urea (metsulfuron-methyl), 1-(4,6-dimethoxypyrimidin-2-yl)-3-mesyl(methyl)sulfamoylurea (amidosulfuron), 2',4'-difluoro-2-(α,α,α-trifluoro-m-tolyloxy)nicotinanilide (diflufenican), 3-(4-isopropylphenyl)-1,1-dimethylurea (isoproturon), 2,6-bis(4,6-dimethoxypyrimidin-2-yloxy)benzoic acid (bispyribac) and salts thereof, N-(phosphonomethyl)glycine (glyphosate) and salts thereof, 4-[hydroxy(methyl)phosphinoyl]-DL-homoalanine (glufosinate) and salts thereof, and 4-[hydroxy(methyl)phosphinoyl]-L-homoalanyl-L-alanyl-L-alanine (bilanafos) and salts thereof and a weed-controlling method characterized by removing weeds by spraying the herbicide composition to paddy fields, lawns, dry fields, or non-agricultural lands.

In the following description, the compounds as the component (B) may be referenced by their common names for convenience.

BEST MODE FOR PRACTICING OF THE INVENTION

2-[(4,6-Dimethoxypyrimidin-2-yl)hydroxymethyl]-6-methoxymethyl-N-difluoromethanesulfonylanilide to be used as the component (A) in the herbicide composition of the invention is a compound excellent in an weed-controlling effect in a low concentration and having a wide herbicide spectrum (Japanese Patent Application Laid-Open No. 2000-44546) but, however, it is needed to dispense it in a high concentration to prevent growth of weeds having grown to an advanced state and perennial weeds and remove them and in the case of its use in a high concentration, there occurs a problem that the safety of valuable cultivated plants such as rice, barley and wheat, etc., lawn grasses and the like is degraded.

However, in the case of its use in combination with either one of more than 20 kinds of the compounds to be used as the component (B) aforementioned, even if it be used in a low concentration, an excellent weed-controlling effect even on weeds grown to an advanced state and perennial weeds can be achieved and dispensation can be carried out safely for rice, barley and wheat, etc. as well as lawn grasses.

Among the compounds to be used as the component (B), propanil, carfentrazone-ethyl, cyhalofop-butyl, fenoxaprop-(P)-ethyl, fenoxapropethyl, profoxydim, sethoxydim, bispyribac and salts thereof, pyribenzoxim, cinmethylin, and quinclorac are commonly used as herbicides in paddy fields; orbencarb, bensulide, asulam, siduron, prodiamine, pendimethalin, benfluralin, carfentrazone-ethyl, and cinmethylin as herbicides in lawns; metsulfuron-methyl, amidosulfuron, diflufenican and isoproturon as herbicides in dry fields or, particularly, in dry fields for barley and wheat, etc.; and glyphosate, glufosinate and bilanaphos as herbicides in non-agricultural lands. It is difficult with any one alone of these chemical compounds to prevent growth of and to remove all kinds of weeds such as weeds of the family of Gramineae, wide-leaf perennial weeds, perennial weeds of the family of Cyperaceae, and the like simultaneously from the time before development of these weeds to the time of the growth. Further, to prevent growth of weeds having grown to an advanced state and perennial weeds or remove them, dispensation of the chemical agents in a high concentration is required and in the case of use of them in a high concentration, there occurs a problem that the safety of valuable cultivated plants such as rice, barley and wheat, etc., and lawn grasses is degraded.

With respect to the herbicide composition of the invention, the component (B) is used in combination with the component (A).

Use of the herbicide composition of the invention exhibits a weed-controlling effect quickly as compared with that in the case where each alone of the components is used and weed-controlling can be quickly performed. Moreover, the herbicide composition shows a weed-controlling effect so high as not to be obtained with one of the respective agents containing a single kind of the compounds.

In the case where the herbicide composition of the invention is used as a herbicide in paddy fields, lawns, dry fields, or non-agricultural lands, above all, as a herbicide in paddy fields or for rice (*Oryza sativa*), it has a wide range of proper chemical agent treatment period as compared with that of known herbicides, especially, a herbicide in paddy fields or for rice, shows a high weed-controlling activity on not only common weeds but also hardly destroyable weeds from the time before the budding of weeds to the time of the developing period, so that it is capable of suppressing propagation of weeds for a long term without or with little inhibition of the growth of cultivated plants.

That is, the herbicide composition of the invention can prevent growth of and remove weeds in the wide range for a long term from the time before the budding of the weeds to the time of the developing period and shows high safety to valuable cultivated plants such as rice, barley and wheat, etc., lawn grasses and others. The target weeds include, for example, in paddy fields, as annual weeds, weeds of the family of Gramineae including *Echinochloa* species such as early watergrass (*Echinochloa oryzicola*), barnyardgrass (*Echinochloa crus-galli* var. *crus-galli*) and the like and AZEGAYA (*Leptochloa chinensis*); *Cyperus* species such as smallflower umbrella plant (*Cyperus difformis*), HINA-GAYATSURI (*Cyperus flaccidus*) and the like; weeds of the family of Pontederiaceae such as heartshape false pickerelweed (*Monochoria vaginalis*), MIZU-AOI (*Monochoria korsakowii*) and the like; weeds of the family of Scrophulariaceae such as *Linderina* species, dopatrium (*Dopatrium junceum*) and the like; weeds of the family of Lythraceae such as indian toothcup (*Rotala indica*), HIME-MISO-HAGI (*Ammannia multiflora*) and the like; MIZO-HA-KOBE (*Elatine triandra*) and others; as well as, as perennial weeds, weeds of the family of Alismataceae such as URIKAWA (*Sagittaria pygmaea*), arrow head (*Sagittaria trifolia*) and the like; weeds of the family of Cyperaceae such as MIZU-GAYATSURI (*Cyperus serotinus*), SHIZUI (*Scirpus nipponicus*), KUROGUWAI (*Eleocharis kuroguwai*), INU-HOTARU-I (*Scirpus juncoides*), KOUKIYA-GARA (*Scirpus planiculmis*), needle spikerush (*Eleocharis acicularis*) and the like; roundleaf pondweed (*Potamogeton distinctus*); SERI (*Oenanthe javanica*) and others; and in lawns, dry fields and orchards, weeds of the family of Gramineae such as *Echinochloa* species, *Digitaria* species, *Setaria* species, annual bluegrass (*Poa annua*), blackgrass (*Alopecurus myosuroides*), goosegrass (*Eleusine indica*) and the like; weeds of the family of Compositae such as annual fleabane (*Erigeron annuus*), philadelphia fleabane (*Erigeron philadelphicus*), broad-leaved fleabane (*Erigeron floribundus*) and the like; weeds of the family of Cyperus such as purple nutsedge (*Cyperus rotundus*), yellow nutsedge (*Cyperus esculentus*), HIMEKUGU (*Cyperus brevifolius*), KAYATSURI GUSA (*Cyperus microiria*) and the like; weeds of the family of Chenopodiaceae such as common lambsquarters (*Chenopodium album*) and the like; weeds of the family of Caryophyllaceae such as MIMINAGUSA (*Cerastium holosteoides*), common chickweed (*Stellaria media*) and the like; weeds of the family of Scrophulariaceae such as *Veronica* species; weeds of the family of Polygonaceae such as *Polygonum* species including OOINUTADE (*Polygonum lapathifolium*) and the like and *Rumex* species; weeds of the family of Amaranthaceae such as slender amaranth (*Amaranthus viridis*), livid amaranth (*Amaranthus lividus*) and the like; weeds of the family of Lamiaceae such as henbit (*Lamium amplexicaule*) and the like; weeds of the family of Rubiaceae such as catchweed bedstraw (*Galium spurium*) and the like; weeds of the family of Commelinaceae such as common dayflower (*Commelina communis*), tropical spiderwort (*Commelina benghalensis*) and the like; weeds of the family of Equisetaceae such as field horsetail (*Equisetum arvense*), marsh horsetail (*Equisetum palustre*) and the like; weeds of the family of Euphorbiaceae such as *Euphorbia* species; weeds of the family of Umbelliferae such as *Hydrocotyle* species; and others.

The mixing ratio of the components (A) and (B) in the herbicide composition of the invention is preferably made different depending on the types and states of weeds, the dispensation period and method, formulation forms and the like and in general, per 1 part by mass of the component (A), the component (B) may be taken in the range of 0.1 to 2,000 parts by mass, preferably 0.2 to 1,500 parts by mass, and more preferably 0.5 to 1,000 parts by mass.

With regard to the mixing ratio of the particular compounds as the component (B) to the component (A), per 1 part by mass of the component (A), preferable amounts of the component (B) compounds to be taken include 0.1 to 10 parts by mass of metsulfuron-methyl, 0.2 to 20 parts by mass of bispyribac or salts thereof, pyribenzoxim or amidosulfuron, 0.5 to 50 parts by mass of profoxydim or sethoxydim, 0.5 to 100 parts by mass of fenoxaprop-(P)-ethyl, fenoxaprop-ethyl or diflufenican, 1 to 200 parts by mass of glyphosate, glufosinate or bilanafos, 3 to 200 parts by mass of pendimethalin, cinmethylin, benfluralin or bensulide, 5 to 300 parts by mass of orbencarb, prodiamine, cyhalofop-butyl or carfentrazone-ethyl, 10 to 1000 parts by mass of asulam, siduron or isoproturon and 50 to 1000 parts by mass of propanil.

As the component (B), the above-mentioned various compounds may be used singly or two or more of them can be selected and used in combination.

The particularly preferable ones as the component (B) include metsulfuron-methyl, bispyribac or salts thereof, amidosulfuron, diflufenican, fenoxaprop-(P)-ethyl, fenoxaprop-ethyl, orbencarb, prodiamine, pendimethalin, benfluralin, siduron, isoproturon and propanil.

The herbicide composition of the invention may contain an insecticide, a fungicide, and other herbicides as well as plant growth adjustment agents, fertilizers and the like according to need.

At the time of dispensation, with respect to the herbicide composition of the invention, only effective components may be used as such, but it is preferable to use them with a carrier, a surfactant, a dispersant, an auxiliary agent and the like, which are used conventionally in formulations, in a form of a powder agent, a hydrated agent, a hydrated granular agent, a flowable agent, an emulsified agent, a liquid agent, a finely granulated agent, a granulated agent and the like.

As the carrier used for the formulations, for example, solid carriers of talc, bentonite, clay, kaolin, diatomaceous earth, fumed silica (white carbon), vermiculite, calcium carbonate, slaked lime, silica sand, ammonium sulfate, urea and the like; and liquid carriers of isopropyl alcohol, xylene, cyclohexane, methylnaphthalene, water and the like can be exemplified.

As the surfactant and dispersant, for example, alkylbenzenesulfonic acid salts, alkylnaphthalenesulfonic acid-formaldehyde condensate product salts, alcohol sulfuric acid ester salts, alkylarylsulfonic acid salts, lignin sulfonic acid salts, polyoxyethylene glycol ethers, polyoxyethylene alkylaryl ethers, polyoxyethylene sorbitan monoalkylate and the like can be named as examples.

As the auxiliary agent, for example, carboxymethylcellulose, polyethylene glycol, gum Arabic and the like can be named as examples.

At the time of using the herbicide composition of the invention, it may be used either directly or may be diluted to a concentration depending on the use purpose and used for stems-and-leaves treatment by spraying to soil or water surface.

The amounts of the effective components in a formulation of the herbicide composition of the invention are properly selected based on the necessity. For example, they are selected from a range of 0.01 to 80% by mass, preferably 0.05 to 50% by mass, in the case of a powder agent, a finely granular agent, or a granular agent and from a range of 1 to 90% by mass, preferably 5 to 80% by mass, in the case of an emulsified agent, a liquid agent, a flowable agent, or a hydrated agent.

The dispensation amount of the herbicide composition of the invention differs depending on the types of the component (B) in the effective components; the target weeds to be removed; the growing tendency of the target weeds; the environmental conditions; formulations and the like.

For example, in the case of a powder agent, a finely granular agent or a granular agent, the total amount of the components (A) and (B) is selected in the range of 0.1 g to 5 kg or, preferably, 1 g to 1 kg, per 10 ares area.

In the case of dispensing an emulsified agent, a liquid agent, a flowable agent or a hydrated agent after dilution with water, the total concentration of the components (A) and (B) at the time of dispensation is selected usually in a range of 10 to 500,000 ppm or, preferably, 10 to 100,000 ppm.

Hereinafter, the invention will be described in more detail by way of Examples, but it is not intended that the present invention be limited to the following embodiments. The types of effective components and additives, the mixing ratios and the like are not limited to these Examples and various modifications may occur to those skilled in the art without deviating from the scope of the invention.

The term "parts" means "parts by mass" in the following description.

EXAMPLE 1

A hydrated agent was prepared by mixing 1 part of 2-[(4,6-dimethoxy-pyrimidin-2-yl)hydroxymethyl]-6-methoxymethyl-N-difluoromethanesulfonylanilide (hereinafter, referred to as Compound A), 12 parts of carfentrazone-ethyl, 0.5 part of polyoxyethylene octylphenyl ether, 0.5 part of β-naphthalenesulfonic acid-formalin condensate sodium salt, 20 parts of diatomaceous earth, and 66 parts of clay and pulverizing the blend thus obtained.

EXAMPLE 2

A hydrated agent was prepared by mixing 2 parts of Compound A, 20 parts of fenoxaprop-ethyl, 0.5 part of polyoxyethylene octylphenyl ether, 0.5 part of β-naphthalenesulfonic acid-formalin condensate sodium salt, 20 parts of diatomaceous earth, 5 parts of fumed silica (white carbon), and 52 parts of clay and pulverizing the blend thus obtained.

EXAMPLE 3

A hydrated agent was prepared by mixing 1 part of Compound A, 10 parts of pendimethalin, 0.5 part of polyoxyethylene octylphenyl ether, 0.5 part of β-naphthalenesulfonic acid-formalin condensate sodium salt, 20 parts of diatomaceous earth, 5 parts of fumed silica (white carbon), and 63 parts of calcium carbonate and pulverizing the blend thus obtained.

EXAMPLE 4

A hydrated granular agent was prepared by adding 5 parts of sodium lignin sulfonate, 1 part of polyoxyethylene alkylaryl ether, 3 parts of sodium polycarboxylate, 5 parts of fumed silica (white carbon), 1 part of α-starch, 65 parts of calcium carbonate and 10 parts of water to 10 parts of Compound A and 10 parts of profoxydim, mixing and kneading the blend thus obtained, extrusion-granulating the mixture, and drying the thus obtained granular product by a fluidized bed dryer.

EXAMPLE 5

A flowable agent was prepared by adding 5 parts of Compound A, 10 parts of bispyribac sodium salt, 2 parts of sodium lignin sulfonate, 4 parts of polyoxyethylene alkylaryl ammonium sulfate, 0.5 part of polyoxyethylene alkylaryl ether, 0.1 part of xanthan gum, 0.5 part of bentonite, and 10 parts of ethyleneglycol to 67.9 parts of water, mixing the thus obtained mixture by a high speed agitator, and pulverizing the mixed mixture by a wet pulverizer.

EXAMPLE 6

A granular agent was prepared by adding 10 parts of water to 1 part of Compound A, 14 parts of orbencarb, 70 parts of an extender which was a mixture of talc and bentonite at 1:3 ratio, 10 parts of fumed silica (white carbon), 5 parts of a mixture of polyoxyethylene sorbitan alkylate, polyoxyethylene alkylaryl polymer and alkylaryl sulfonate, thoroughly mixing and kneading the thus obtained mixture to obtain a pasty mixture, extruding the mixture through a screen of 1 mm mesh opening, drying the extruded mixture, and then chopping the thus obtained product in a 0.5 to 1 mm length.

In the following, the effects of the respective herbicide compositions of the invention will be described by way of the Test Examples.

TEST EXAMPLE 1

Weed-Controlling Effect Test on Direct-Sowing Paddy-Rice by Stems-and-Leaves Treatment Paddy field soil was packed in a plastic pot with a 1/2000 are surface area, respective seeds of *Oryza sativa* (Or), *Echinochloa oryzicola* (Eo), *Digitaria ciliaris* (Di), and *Leptochloa chinensis* (Le) were sowed and water was supplied from the bottom part of the pot. Paddy field soil was packed in another plastic pot with a 1/2000 are surface area, water was introduced into the pot, and the soil was shuffled. After that, tuberous roots of *Cyperus esculentus* (Cy) and *Sagittaria trifolia* (Sa) were buried in the soil and immersed in water in 1 cm depth. The plants were grown at an average temperature of around 23 to 25° C. outdoors and when the *Echinochloa oryzicola* grew to the 2.5 leaves stage, specified amounts of the hydrated agents prepared in the same manner as in Example 1 diluted with water were sprayed to whole plants for stems-and-leaves treatment. After that, plants growth was carried out outdoors and the air-dried weights of the respective plant bodies above the soil were measured on the 28th day after the treatment, and the weed-controlling effects and the phytotoxicities of the agents were shown as indexes on the basis of the criteria as shown in Table 1. The results are shown in Table 2. The dosages were indicated on the basis of the amounts of the effective components per 10 ares area.

TABLE 1

| Index | Weed-controlling effect and phytotoxicity degree of agent (Growth inhibition degree in portions above soil) |
| --- | --- |
| 10 | 95% or higher growth inhibition |
| 9 | Not less than 85% but less than 95% growth inhibition |
| 8 | Not less than 75% but less than 85% growth inhibition |
| 7 | Not less than 65% but less than 75% growth inhibition |
| 6 | Not less than 55% but less than 65% growth inhibition |
| 5 | Not less than 45% but less than 55% growth inhibition |
| 4 | Not less than 35% but less than 45% growth inhibition |
| 3 | Not less than 25% but less than 35% growth inhibition |
| 2 | not less than 15% but less than 25% growth inhibition |
| 1 | not less than 5% but less than 15% growth inhibition |
| 0 | not less than 0% but less than 5% growth inhibition |

TABLE 2

| Compounds tested | Dosages, gai/10 ares | Weed-controlling effect | | | | | Phytotoxicity |
| --- | --- | --- | --- | --- | --- | --- | --- |
| | | Eo | Di | Le | Cy | Sa | Or |
| Compound A + propanil | 0.5 + 300 | 10 | 10 | 10 | 8 | 10 | 0 |
| propanil | 300 | 5 | 7 | 6 | 1 | 2 | 0 |
| Compound A + cyhalofop-butyl | 0.5 + 20 | 10 | 10 | 10 | — | — | 0 |
| cyhalofop-butyl | 20 | 9 | 8 | 9 | — | — | 0 |
| Compound A + carfentrazone-ethyl | 0.5 + 6 | 10 | 5 | — | 8 | 10 | 0 |
| carfentrazone-ethyl | 6 | 4 | 3 | — | 1 | 9 | 2 |
| Compound A + fenoxaprop-ethyl | 0.5 + 5 | 10 | 10 | 10 | — | — | 1 |
| fenoxaprop-ethyl | 5 | 10 | 10 | 10 | — | — | 5 |
| Compound A + profoxydim | 0.5 + 0.5 | 10 | 10 | 10 | — | — | 0 |
| profoxydim | 0.5 | 10 | 8 | 9 | — | — | 1 |
| Compound A + sethoxydim | 0.5 + 1 | 10 | 10 | 10 | — | — | 0 |
| sethoxydim | 1 | 9 | 7 | 8 | — | — | 1 |
| Compound A + bispyribac sodium salt | 0.5 + 1.5 | 10 | 5 | 6 | 10 | 10 | 0 |
| bispyribac sodium salt | 1.5 | 8 | 1 | 1 | 3 | 8 | 0 |
| Compound A + pyribenzoxim | 0.5 + 2 | 10 | 6 | 6 | 10 | 10 | 0 |
| pyribenzoxim | 2 | 8 | 2 | 1 | 5 | 7 | 0 |
| Compound A + quinclorac | 0.5 + 12.5 | 10 | 4 | 2 | 9 | 10 | 0 |
| quinclorac | 12.5 | 10 | 3 | 1 | 2 | 3 | 0 |
| Compound A | 0.5 | 7 | 0 | 0 | 5 | 8 | 0 |

TEST EXAMPLE 2

Weed-controlling Effect Test on Lawn Weeds by Soil Treatment

A dry-field soil was packed in a 15 cm by 25 cm plastic pot of 10 cm height and *Zoysia tenuifolia Willd.* (Zo) separately grown for 1 year was implanted and respective seeds of *Digitaria ciliaris* (Di), *Setaria viridis* (Se), *Chenopodium album* (Ch), and *Polygonum lapathifolium* (Po), and *Amaranthus viridis* (Am) were sowed and water irrigation was carried out. On the next day, specified amounts of the hydrated agents prepared in the same manner as in Example 1 diluted with 100 liters of water were sprayed per 10 ares evenly over the soil surface and stems and leaves of *Zoysia tenuifolia Willd.* After that, plants growth was carried out in a greenhouse and the air-dried weights of the respective plant bodies above the soil were measured on the 20th day after the treatment and the weed-controlling effects and the phytotoxicities of the agents were shown as indexes on the basis of the criteria as shown in Table 1. The results are shown in Table 3. The dosages were indicated on the basis of the amounts of the effective components per 10 ares area.

TABLE 3

| Compounds tested | Dosages, gai/10 ares | Weed-controlling effect | | | | | Phytotoxicity |
|---|---|---|---|---|---|---|---|
| | | Di | Se | Ch | Po | Am | Zo |
| Compound A + orbencarb | 2 + 50 | 10 | 10 | 10 | 10 | 10 | 0 |
| Orbencarb | 50 | 8 | 9 | 0 | 0 | 1 | 0 |
| Compound A + siduron | 2 + 100 | 10 | 10 | 10 | 10 | 10 | 0 |
| Siduron | 100 | 9 | 9 | 6 | 4 | 3 | 0 |
| Compound A + prodiamine | 2 + 50 | 10 | 10 | 10 | 10 | 10 | 0 |
| Prodiamine | 50 | 9 | 8 | 5 | 4 | 5 | 0 |
| Compound A + pendimethalin | 2 + 20 | 10 | 10 | 10 | 10 | 10 | 0 |
| Pendimethalin | 20 | 7 | 6 | 3 | 3 | 4 | 0 |
| Compound A + benfluralin | 2 + 70 | 10 | 10 | 10 | 10 | 10 | 0 |
| Benfluralin | 70 | 9 | 9 | 5 | 6 | 5 | 0 |
| Compound A + cinmethylin | 2 + 20 | 10 | 10 | 10 | 10 | 10 | 0 |
| Cinmethylin | 20 | 9 | 8 | 3 | 1 | 3 | 0 |
| Compound A | 2 | 5 | 3 | 7 | 8 | 7 | 0 |

TEST EXAMPLE 3

Weed-controlling Effect Test by Stems-and-leaves Treatment

A dry-field soil was packed in a plastic pot with 1/2000 are surface area, respective seeds of *Echinochloa crus-galli* var. *crus-galli* (Ec), *Digitaria ciliaris* (Di), *Polygonum lapathifolium* (Po), *Amaranthus viridis* (Am) and *Chenopodium album* (Ch) were sowed and water was supplied from the bottom part of the pot. The plants were grown at an average temperature of around 23 to 25° C. in a greenhouse and when the *Echinochloa crus-galli* var. *crus-galli* reached the 3.5 leaves stage, specified amounts of the hydrated agents prepared in the same manner as in Example 1 diluted with water were sprayed to entire plants for stems-and-leaves treatment. After that, plants growth was carried out again in the greenhouse and the air-dried weights of the respective plant bodies above the soil were measured on the 20th day after the treatment and the weed-controlling effects and the phytotoxicities of the agents were shown as indexes on the basis of the criteria as shown in Table 1. The results are shown in Table 4. The dosages were indicated on the basis of the amounts of the effective components per 10 ares area.

TABLE 4

| Compounds tested | Dosages, gai/10 ares | Weed-controlling effect | | | | |
|---|---|---|---|---|---|---|
| | | Ec | Di | Po | Am | Ch |
| Compound A + glyphosate ammonium salt | 1 + 5 | 10 | 10 | 10 | 10 | 10 |
| glyphosate ammonium salt | 5 | 7 | 8 | 2 | 8 | 6 |
| Compound A + glufosinate ammonium salt | 1 + 8 | 10 | 10 | 10 | 10 | 10 |
| glufosinate ammonium salt | 8 | 5 | 9 | 6 | 8 | 9 |
| Compound A + bilanafos sodium salt | 1 + 4 | 10 | 10 | 10 | 10 | 10 |
| bilanafos sodium salt | 4 | 4 | 7 | 6 | 5 | 3 |
| Compound A + asulam | 1 + 80 | 10 | 10 | 10 | 10 | 10 |

TABLE 4-continued

| Compounds tested | Dosages, gai/10 ares | Weed-controlling effect | | | | |
|---|---|---|---|---|---|---|
| | | Ec | Di | Po | Am | Ch |
| Asulam | 80 | 8 | 7 | 0 | 2 | 2 |
| Compound A | 1 | 4 | 6 | 8 | 7 | 7 |

TEST EXAMPLE 4

Weed-controlling Effect Test on Wheat by Stems-and-leaves Treatment

A dry-field soil was packed in a plastic pot with 1/2000 are surface area, respective seeds of wheat (*Triticum aestivum*) (Tr), *Alopecurus myosuroides* (Al), *Poa annua* (Pa), *Stellaria media* (St), *Lamium amplexicaule* (La) and *Galium spurium* (Ga) were sowed and water was supplied from the bottom part of the pot. The plants were grown at an average temperature of around 15 to 17° C. in a greenhouse and when wheat reached the 3.5 leaves stage, specified amounts of the hydrated agents prepared in the same manner as in Example 2 diluted with water were sprayed to entire plants for stems-and-leaves treatment. After that, plants growth was carried out again in the greenhouse and the air-dried weights of the respective plant bodies above the soil were measured on the 30th day after the treatment and the weed-controlling effects and the phytotoxicities of the agents were shown as indexes on the basis of the criteria as shown in Table 1. The results are shown in Table 5. The dosages were shown on the basis of the amounts of the effective components per 10 ares area.

TABLE 5

| Compounds tested | Dosages, gai/10 ares | Weed-controlling effect | | | | | Phytotoxicity |
|---|---|---|---|---|---|---|---|
| | | Al | Pa | St | La | Ga | Tr |
| Compound A + bispyribac sodium salt | 3 + 1.5 | 9 | 10 | 10 | 10 | 10 | 0 |
| bispyribac sodium salt | 1.5 | 6 | 8 | 8 | 7 | 8 | 0 |
| Compound A + fenoxaprop-ethyl | 3 + 4 | 10 | 9 | 8 | 8 | 7 | 0 |
| fenoxaprop-ethyl | 4 | 8 | 0 | 0 | 0 | 0 | 0 |
| Compound A + metsulfuron-methyl | 3 + 0.4 | 9 | 9 | 10 | 10 | 8 | 0 |
| metsulfuron-methyl | 0.4 | 0 | 3 | 8 | 8 | 3 | 0 |
| Compound A + amidosulfuron | 3 + 1.5 | 9 | 9 | 8 | 8 | 8 | 0 |
| amidosulfuron | 1.5 | 0 | 0 | 2 | 0 | 8 | 0 |
| Compound A + diflufenican | 3 + 4 | 8 | 8 | 10 | 10 | 10 | 0 |
| diflufenican | 4 | 0 | 0 | 5 | 5 | 6 | 0 |
| Compound A + isoproturon | 3 + 75 | 10 | 10 | 9 | 8 | 8 | 0 |
| isoproturon | 75 | 9 | 7 | 3 | 0 | 0 | 0 |
| Compound A | 3 | 6 | 7 | 4 | 3 | 4 | 0 |

INDUSTRIAL APPLICABILITY

Owing to a synergistic effect of the effective components; 2-[(4,6-dimethoxypyrimidin-2-yl)hydroxymethyl]-6-methoxymethyl-N-difluoromethanesulfonylanilide and at least one compound selected from orbencarb, bensulide, asulam, propanil, carfentrazone-ethyl, siduron, prodiamine, pendimethalin, benfluralin, cyhalofop-butyl, fenoxaprop-(P)-ethyl, fenoxaprop-ethyl, profoxydim, sethoxydim, pyribenzoxim, cinmethylin, quinclorac, metsulfuron-methyl, amidosulfuron, diflufenican, isoproturon, bispyribac and salts thereof, glyphosate and salts thereof, glufosinate and salts thereof, and bilanafos and salts thereof, the herbicide compositions of the invention exhibit quick weed-controlling effects and are capable of carrying out weed-controlling. The compositions show high weed-controlling effects even in a low effective component concentration and at the same time have a wide herbicide spectrum.

When a herbicide composition of the invention is used as a herbicide for paddy fields, lawns, dry fields, or non-agricultural lands, above all, as a herbicide in paddy fields or for rice, it has a wide range of proper chemical agent treatment period as compared with that of known herbicides, shows a high weed-controlling activity on hardly destroyable weeds from the days before budding of weeds to the time of the developing period, and suppresses propagation of weeds for a long term without or with little inhibition of the growth of valuable cultivated plants.

That is, the herbicide composition of the invention can prevent growth of and remove annual weeds such as early watergrass (*Echinochloa oryzicola*), barnyardgrass (*Echinochloa crus-galli* var. *crus-galli*), smallflower umbrella plant (*Cyperus difformis*), HINA-GAYATSURI (*Cyperus flaccidus*), heartshape false pickerelweed (*Monochoria vaginalis*), MIZU-AOI (*Monochoria korsakowii*), *Linderina* species, dopatrium (*Dopatrium junceum*), indian toothcup (*Rotala indica*), MIZO-HAKOBE (*Elatine triandra*), HIME-MISO-HAGI (*Ammannia multiflora*) and the like, and perennial weeds such as URIKAWA (*Sagittaria pygmaea*), arrow head (*Sagittaria trifolia*) and the like, round-leaf pondweed (*Potamogeton distinctus*), SERI (*Oenanthe javanica*), MIZU-GAYATSURI (*Cyperus serotinus*), SHIZUI (*Scirpus nipponicus*), KUROGUWAI (*Eleocharis kuroguwai*), INU-HOTARU-I (*Scirpus juncoides*), KOUKIYAGARA (*Scirpus planiculmis*), needle spikerush (*Eleocharis acicularis*) and the like for a long term from the days before budding of the weeds to the time of the developing period.

Moreover, the herbicide composition of the invention is highly safe to valuable cultivated plants, especially to rice, barley and wheat, lawn grasses and others.

The invention claimed is:

1. A herbicide composition which comprises, as a blend,
   (A) 2-[(4,6-dimethoxypyrimidin-2-yl)hydroxymethyl]-6-methoxymethyl-N-difluoromethanesulfonylanilide and
   (B) a compound selected from the group consisting of
   (1) S-2-chloro-benzyl diethyl-thiocarbamate (orbencarb),
   (2) S-2-benzenesulfonamidoethyl O,O-diisopropyl phosphorodithioate (bensulide),
   (3) methyl sulfanilylcarbamate (asulam),
   (4) 3',4'-dichloropropionanilide (propanil),
   (5) ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl),
   (6) 1-(2-methylcyclohexyl)-3-phenylurea (siduron),
   (7) 5-dipropyl-amino-α,α,α-trifluoro-4,6-dinitro-o-toluidine (prodiamine),
   (8) N-(1-ethylpropyl)-2,6-dinitro-3,4-xylidine (pendimethalin),
   (9) N-butyl-N-ethyl-α,α,α-trifluoro-2,6-dinitro-p-toluidine (benfluralin),
   (10) butyl (R)-2-[4-(4-cyano-2-fluorophenoxy)phenoxy]propionate (cyhalofopbutyl),
   (11) ethyl (R)-2-[4-(6-chlorobenzoxazol-2-yloxy)phenoxy]propionate (fenoxaprop-(P)-ethyl),
   (12) ethyl(±)-2-[4-(6-chlorobenzoxazol-2-yloxy)-phenoxy]propionate (fenoxaprop-ethyl),
   (13) 2-{1-[2-(4-chlorophenoxy)propoxyimino]butyl}-3-hydroxy-5-(thian-3-yl)cyclohex-2-enone (profoxydim),
   (14) (±)-(EZ)-2-(1-ethoxyiminobutyl)-5-[2-(ethylthio)propyl]-3-hydroxycyclohex-2-enone (sethoxydim),
   (15) benzophenone O-[2,6-bis(4,6-dimethoxy-pyrimidin-2-yloxy)benzoyl]oxime (pyribenzoxim),
   (16) (1RS,2SR,4SR)-1,4-epoxy-p-menth-2-yl 2-methylbenzyl ether (cinmethylin),
   (17) 3,7-dichloroquinoline-8-carboxylic acid (quinclorac),
   (18) N-(4-methoxy-6-methyl-1,3,5-triazin-2-yl)-N'-(2-methoxycarbonyl-phenylsulfonyl)urea (metsulfuron-methyl),
   (19) 1-(4,6-dimethoxypyrimidin-2-yl)-3-mesyl(methyl)sulfamoylurea (amidosulfuron),
   (20) 2',4'-difluoro-2-(α,α,α-trifluoro-m-tolyloxy)nicotinanilide (diflufenican),
   (21) 3-(4-isopropylphenyl)-1,1-dimethylurea (isoproturon),
   (22) 2,6-bis(4,6-dimethoxypyrimidin-2-yloxy)benzoic acid (bispyribac) and salts thereof,
   (23) N-(phosphonomethyl)glycine (glyphosate) and salts thereof,
   (24) 4-[hydroxy(methyl)phosphinoyl]-DL-homoalanine (glufosinate) and salts thereof, and
   (25) 4-[hydroxy(methyl)phosphinoyl]-L-homoalanyl-L-alanyl-L-alanine (bilanafos) and salts thereof.

2. The herbicide composition according to claim 1, wherein the amount of the component (B) is in the range from 0.1 to 2000 parts by mass per part by mass of the component (A).

3. The herbicide composition according to claim 1, wherein the component (B) is a compound selected from the group consisting of N-(4-methoxy-6-methyl-1,3,5-triazin-2-yl)-N'-(2-methoxycarbonyl-phenylsulfonyl)urea (metsulfuron-methyl) and 1-(4,6-dimethoxypyrimidin-2-yl)-3-mesyl(methyl)sulfamoylurea (amidosulfuron).

4. The herbicide composition according to claim 1, wherein the component (B) is 2',4'-difluoro-2-(α,α,α-trifluoro-m-tolyloxy)nicotinanilide (diflufenican).

5. The herbicide composition according to claim 1, wherein the component (B) is a compound selected from the group consisting of ethyl (R)-2-[4-(6-chlorobenzoxazol-2-yloxy)phenoxy]propionate (fenoxaprop-(P)-ethyl) and ethyl (±)-2-[4-(6-chlorobenzoxazol-2-yloxy)phenoxy]propionate (fenoxaprop-ethyl).

6. The herbicide composition according to claim 1, wherein the component (B) is a compound selected from the group consisting of 2-{1-[2-(4-chlorophenoxy)propoxyimino]butyl}-3-hydroxy-5-(thian-3-yl)cyclohex-2-enone (profoxydim) and (±)-(EZ)-2-(1-ethoxyiminobutyl)-5-[2-(ethylthio)propyl]-3-hydroxycyclohex-2-enone (sethoxydim).

7. The herbicide composition according to claim 1, wherein the component (B) is a compound selected from the group consisting of 2,6-bis(4,6-dimethoxypyrimidin-2-yloxy)benzoic acid (bispyribac) and salts thereof.

8. The herbicide composition according to claim 1, wherein the component (B) is benzophenone O-[2,6-bis(4,6-dimethoxypyrimidin-2-yloxy)benzoyl]oxime (pyribenzoxim).

9. The herbicide composition according to claim 1, wherein the component (B) is a compound selected from the group consisting of 4-[hydroxy(methyl)phosphinoyl]-L-homoalanyl-L-alanyl-L-alanine (bilanafos), 4-[hydroxy(methyl)phosphinoyl]-DL-homoalanine (glufosinate) and salts thereof.

10. The herbicide composition according to claim 1, wherein the component (B) is a compound selected from the group consisting of N-(phosphonomethyl)glycine (glyphosate) and salts thereof.

11. The herbicide composition according to claim 1, wherein the component (B) is a compound selected from the group consisting of N-(1-ethylpropyl)-2,6-dinitro-3,4-xylidine (pendimethalin) and N-butyl-N-ethyl-α,α,α-trifluoro-2,6-dinitro-p-toluidine (benfluralin).

12. The herbicide composition according to claim 1, wherein the component (B) is (1RS,2SR,4SR)-1,4-epoxy-p-menth-2-yl 2-methylbenzyl ether (cinmethylin).

13. The herbicide composition according to claim 1, wherein the component (B) is ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl).

14. The herbicide composition according to claim 1, wherein the component (B) is 3-(4-isopropylphenyl)-1,1-dimethylurea (isoproturon).

15. The herbicide composition according to claim 1, wherein the component (B) is S-2-chloro-benzyl diethylthiocarbamate (orbencarb).

16. The herbicide composition according to claim 1, wherein the component (B) is 5-dipropylamino-α,α,α-trifluoro-4,6-dinitro-o-toluidine (prodiamine).

17. The herbicide composition according to claim 1, wherein the component (B) is 3,7-dichloroquinoline-8-carboxylic acid (quinclorac).

18. The herbicide composition according to claim 1, wherein the component (B) is 1-(2-methylcyclohexyl)-3-phenylurea (siduron).

19. The herbicide composition according to claim 1, wherein the component (B) is methyl sulfanilylcarbamate (asulam).

20. The herbicide composition according to claim 1, wherein the component (B) is 3',4'-dichloropropionanilide (propanil).

21. A method for controlling growth of weeds in a land which comprises the step of sprinkling the herbicide composition defined in claim 1 over the land where the weeds grow.

22. The method for controlling growth of weeds in a land according to claim 21, wherein the amount of the herbicide composition sprinkled over the land in the form of a powder agent, finely granulated agent or granulated agent is in the range from 0.1 g to 5 kg as the total amounts of the components (A) and (B) per 10 ares area of the land.

23. The method for controlling growth of weeds according to claim 21, wherein the concentration of the components (A) and (B) as a total in the herbicide composition in the form of an emulsified agent, liquid agent, flowable agent or hydrated agent is in the range from 10 to 500,000 ppm by mass.

* * * * *